(12) United States Patent
Deem et al.

(10) Patent No.: US 8,504,147 B2
(45) Date of Patent: Aug. 6, 2013

(54) SYSTEMS AND METHODS FOR NEUROMODULATION FOR TREATMENT OF PAIN AND OTHER DISORDERS ASSOCIATED WITH NERVE CONDUCTION

(75) Inventors: Mark E. Deem, Mountain View, CA (US); Hanson S. Gifford, Woodside, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 217 days.

(21) Appl. No.: 12/567,521

(22) Filed: Sep. 25, 2009

(65) Prior Publication Data

US 2010/0010567 A1    Jan. 14, 2010

Related U.S. Application Data

(63) Continuation of application No. 11/459,582, filed on Jul. 24, 2006, now abandoned.

(60) Provisional application No. 60/701,747, filed on Jul. 22, 2005.

(51) Int. Cl.
*A61N 1/00*    (2006.01)
*G01N 21/00*   (2006.01)

(52) U.S. Cl.
USPC .................... 607/2; 607/154; 422/81

(58) Field of Classification Search
USPC ......................... 607/2, 154; 422/81
See application file for complete search history.

(56) References Cited

U.S. PATENT DOCUMENTS

| | | | |
|---|---|---|---|
| 5,300,068 | A | 4/1994 | Rosar et al. |
| 5,484,400 | A | 1/1996 | Edwards et al. |
| 5,599,345 | A | 2/1997 | Edwards et al. |
| 5,672,174 | A | 9/1997 | Gough et al. |
| 5,688,266 | A | 11/1997 | Edwards et al. |
| 5,772,590 | A | 6/1998 | Webster, Jr. |
| 5,893,885 | A | 4/1999 | Webster et al. |
| 5,944,710 | A | 8/1999 | Dev et al. |
| 5,954,719 | A | 9/1999 | Chen et al. |
| 6,135,999 | A | 10/2000 | Fanton et al. |
| 6,219,577 | B1 | 4/2001 | Brown, III et al. |
| 6,292,695 | B1 | 9/2001 | Webster et al. |
| 6,314,325 | B1 | 11/2001 | Fitz |
| 6,322,558 | B1 | 11/2001 | Taylor et al. |
| 6,322,559 | B1 | 11/2001 | Daulton et al. |
| 6,326,177 | B1 * | 12/2001 | Schoenbach et al. ...... 435/173.7 |
| 6,413,255 | B1 | 7/2002 | Stern |

(Continued)

FOREIGN PATENT DOCUMENTS

| | | |
|---|---|---|
| WO | WO-9525472 | 9/1995 |
| WO | WO-9736548 | 10/1997 |

(Continued)

OTHER PUBLICATIONS

U.S. Appl. No. 12/790,639, Wu et al.

(Continued)

*Primary Examiner* — Nicole F Lavert

(57) ABSTRACT

Methods and apparatus are provided for selective destruction or temporary disruption of nerves and/or conduction pathways in a mammalian body for the treatment of pain and other disorders. Apparatus comprises catheters having electrodes for targeting and affecting nerve tissue at a cellular level to reversible and irreversible nerve poration and incapacitation.

16 Claims, 8 Drawing Sheets

U.S. PATENT DOCUMENTS

| | | | |
|---|---|---|---|
| 6,488,679 B1 | 12/2002 | Swanson et al. | |
| 6,616,624 B1 | 9/2003 | Kieval | |
| 6,622,731 B2 | 9/2003 | Daniel et al. | |
| 6,654,636 B1* | 11/2003 | Dev et al. | 604/21 |
| 6,845,267 B2 | 1/2005 | Harrison et al. | |
| 6,862,479 B1* | 3/2005 | Whitehurst et al. | 607/39 |
| 6,939,346 B2 | 9/2005 | Kannenberg et al. | |
| 6,978,174 B2 | 12/2005 | Gelfand et al. | |
| 7,162,303 B2 | 1/2007 | Levin et al. | |
| 7,617,005 B2 | 11/2009 | Demarais et al. | |
| 7,620,451 B2 | 11/2009 | Demarais et al. | |
| 7,647,115 B2 | 1/2010 | Levin et al. | |
| 7,653,438 B2 | 1/2010 | Deem et al. | |
| 7,717,948 B2 | 5/2010 | Demarais et al. | |
| 7,756,583 B2 | 7/2010 | Demarais et al. | |
| 8,131,371 B2 | 3/2012 | Demarais et al. | |
| 8,145,317 B2 | 3/2012 | Demarais et al. | |
| 8,150,519 B2 | 4/2012 | Demarais et al. | |
| 8,150,520 B2 | 4/2012 | Demarais et al. | |
| 8,175,711 B2 | 5/2012 | Demarais et al. | |
| 2002/0127144 A1* | 9/2002 | Mehta | 422/81 |
| 2002/0165532 A1 | 11/2002 | Hill et al. | |
| 2002/0183682 A1 | 12/2002 | Darvish et al. | |
| 2003/0050681 A1 | 3/2003 | Pianca et al. | |
| 2003/0125790 A1 | 7/2003 | Fastovsky et al. | |
| 2003/0181897 A1 | 9/2003 | Thomas et al. | |
| 2003/0199863 A1 | 10/2003 | Swanson et al. | |
| 2003/0216792 A1 | 11/2003 | Levin et al. | |
| 2004/0010289 A1 | 1/2004 | Biggs et al. | |
| 2004/0162590 A1* | 8/2004 | Whitehurst et al. | 607/17 |
| 2004/0215186 A1 | 10/2004 | Cornelius et al. | |
| 2005/0080409 A1 | 4/2005 | Young et al. | |
| 2005/0187579 A1 | 8/2005 | Danek et al. | |
| 2005/0228460 A1 | 10/2005 | Levin et al. | |
| 2005/0234523 A1 | 10/2005 | Levin et al. | |
| 2006/0025821 A1 | 2/2006 | Gelfand et al. | |
| 2006/0041277 A1 | 2/2006 | Deem et al. | |
| 2006/0095029 A1 | 5/2006 | Young et al. | |
| 2006/0206150 A1 | 9/2006 | Demarais et al. | |
| 2006/0212076 A1 | 9/2006 | Demarais et al. | |
| 2006/0212078 A1 | 9/2006 | Demarais et al. | |
| 2006/0235474 A1 | 10/2006 | Demarais | |
| 2006/0265014 A1 | 11/2006 | Demarais et al. | |
| 2006/0265015 A1 | 11/2006 | Demarais et al. | |
| 2006/0271111 A1 | 11/2006 | Demarais et al. | |
| 2006/0276852 A1 | 12/2006 | Demarais et al. | |
| 2007/0066957 A1 | 3/2007 | Demarais et al. | |
| 2007/0083239 A1 | 4/2007 | Demarais et al. | |
| 2007/0129720 A1 | 6/2007 | Demarais et al. | |
| 2007/0129760 A1 | 6/2007 | Demarais et al. | |
| 2007/0129761 A1 | 6/2007 | Demarais et al. | |
| 2007/0135875 A1 | 6/2007 | Demarais et al. | |
| 2007/0173899 A1 | 7/2007 | Levin et al. | |
| 2007/0265687 A1 | 11/2007 | Deem et al. | |
| 2008/0213331 A1 | 9/2008 | Gelfand et al. | |
| 2008/0255642 A1 | 10/2008 | Zarins et al. | |
| 2009/0036948 A1 | 2/2009 | Levin et al. | |
| 2009/0062873 A1 | 3/2009 | Wu et al. | |
| 2009/0076409 A1 | 3/2009 | Wu et al. | |
| 2010/0010567 A1 | 1/2010 | Deem et al. | |
| 2010/0057150 A1 | 3/2010 | Demarais et al. | |
| 2010/0137860 A1 | 6/2010 | Demarais et al. | |
| 2010/0137952 A1 | 6/2010 | Demarais et al. | |
| 2010/0168731 A1 | 7/2010 | Wu et al. | |
| 2010/0168739 A1 | 7/2010 | Wu et al. | |
| 2010/0174282 A1 | 7/2010 | Demarais et al. | |
| 2010/0191112 A1 | 7/2010 | Demarais et al. | |
| 2010/0222851 A1 | 9/2010 | Deem et al. | |
| 2010/0222854 A1 | 9/2010 | Demarais et al. | |
| 2010/0249773 A1 | 9/2010 | Clark et al. | |
| 2010/0268307 A1 | 10/2010 | Demarais et al. | |

FOREIGN PATENT DOCUMENTS

| | | |
|---|---|---|
| WO | WO-0122897 | 4/2001 |
| WO | WO-0170114 | 9/2001 |
| WO | WO-2005110528 | 11/2005 |
| WO | WO-2006022790 A1 | 3/2006 |
| WO | WO-2006041847 | 4/2006 |
| WO | WO-2006041881 | 4/2006 |
| WO | WO-2007008954 | 1/2007 |
| WO | WO-2007035537 | 3/2007 |
| WO | WO-2007078997 A2 | 7/2007 |
| WO | WO-2007086965 | 8/2007 |
| WO | WO-2007103879 | 9/2007 |
| WO | WO-2007103881 | 9/2007 |
| WO | WO-2007121309 | 10/2007 |
| WO | WO-2007146834 | 12/2007 |
| WO | WO-2008003058 | 1/2008 |
| WO | WO-2008061150 | 5/2008 |
| WO | WO-2008061152 | 5/2008 |
| WO | WO-2008070413 | 6/2008 |
| WO | WO-2010078175 A1 | 7/2010 |

OTHER PUBLICATIONS

U.S. Appl. No. 12/871,457, Wu et al.
U.S. Appl. No. 12/940,922, Gelfand et al.
U.S. Appl. No. 12/996,897, Demarais.
U.S. Appl. No. 13/007,370, Gelfand et al.
U.S. Appl. No. 13/009,748, Beetel et al.
U.S. Appl. No. 12/910,631, Wu et al.
International Search Report and Written Opinion for PCT/US2009/069334; Applicant: Ardian, Inc.; Mailing Date: Mar. 1, 2010, 10 pages.
International Search Report and Written Opinion, PCT/US05/35693, Mailed on Mar. 8, 2006, Applicant: Ardian, Inc., 29 pages.
International Search Report and Written Opinion, PCT/US05/35757, Mailed on Dec. 27, 2006, Applicant: Ardian, Inc., 8 pages.
International Search Report and Written Opinion, PCT/US06/36120, Mailed on Jun. 25, 2008, Applicant: Ardian, Inc., 10 pages.
International Search Report and Written Opinion, PCT/US06/41889, Mailed on Oct. 20, 2008, Applicant: Ardian, Inc., 7 pages.
International Search Report and Written Opinion, PCT/US06/48822, Mailed on Aug. 15, 2008, Applicant: Ardian, Inc., 12 pages.
International Search Report and Written Opinion, PCT/US07/63322, Mailed on Mar. 3, 2008, Applicant: Ardian, Inc., 13 pages.
International Search Report and Written Opinion, PCT/US07/63324, Mailed on Oct. 10, 2008, Applicant: Ardian, Inc., 13 pages.
International Search Report and Written Opinion, PCT/US07/66539, Mailed on Jan. 28, 2008, Applicant: Ardian, Inc., 8 pages.
International Search Report and Written Opinion, PCT/US07/70799, Mailed on Jul. 2, 2008, Applicant: Ardian, Inc., 7 pages.
International Search Report and Written Opinion, PCT/US07/72396, Mailed on Aug. 27, 2008, Applicant: Ardian, Inc., 9 pages.
International Search Report and Written Opinion, PCT/US07/84701, Mailed on Aug. 21, 2008, Applicant: Ardian, Inc., 11 pages.
International Search Report and Written Opinion, PCT/US07/84705, Mailed on Jul. 28, 2008, Applicant: Ardian, Inc., 12 pages.
International Search Report and Written Opinion, PCT/US07/84708, Mailed on Aug. 11, 2008, Applicant: Ardian, Inc., 9 pages.
International Search Report, PCT/US04/38498, Mailed Feb. 18, 2005, Applicant: G & L Consulting, LLC, 4 pages.
European Search Report; European Patent Application No. 05806045.0; Applicant: Ardian, Inc.; Date of Mailing: Sep. 22, 2009, 8 pages.
European Search Report; European Patent Application No. 05811851.4; Applicant: Ardian, Inc.; Date of Mailing: Oct. 1, 2009, 7 pages.
European Search Report; European Patent Application No. 06847926.0; Applicant: Ardian, Inc.; Date of Mailing: Feb. 10, 2010, 6 pages.
European Search Report; European Patent Application No. 0775925.8; Applicant: Ardian, Inc.; Date of Mailing: Apr. 29, 2010, 9 pages.
European Search Report; European Patent Application No. 07799148.7; Applicant: Ardian, Inc.; Date of Mailing: Jul. 23, 2009, 6 pages.
European Search Report; European Patent Application No. 09156661.2; Applicant: Ardian, Inc.; Date of Mailing: Jul. 23, 2009, 6 pages.

European Search Report; European Patent Application No. 09167937.3; Applicant: Ardian, Inc.; Date of Mailing: Nov. 11, 2009, 6 pages.
European Search Report; European Patent Application No. 09168202.1; Applicant: Ardian, Inc.; Date of Mailing: Nov. 11, 2009, 5 pages.
European Search Report; European Patent Application No. 09168204.7; Applicant: Ardian, Inc.; Date of Mailing: Nov. 19, 2009, 6 pages.
European Search Report; European Patent Application No. 07868755.5; Applicant: Ardian, Inc.; Date of Mailing: Jul. 28, 2010, 7 pages.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
Avitall et al., "The creation of linear contiguous lesions in the atria with an expandable loop catheter," Journal of the Americam College of Cardiology, 1999; 33; pp. 972-984.
Benito, F., et al. "Radiofrequency cateheter ablation of accessory pathways in infants." Heart, 78:160-162 (1997).
Curtis, J.J., et al., "Surgical therapy for presistent hypertension after renal transplantation." Trasnplantation, 31: 125-128.
Dibona, G.F. "Sympathetic nervous system and kidney in hypertension." Nephrol and Hypertension, 11: 197-200 (2002).
Dibona, G.F., et al. "Neural control of renal function." Physiol Rev, 77:75-197 (1997).
Dubuc, M., et al., "Feasibility of cardiac cryoablation using a transvenous steerable electrode catheter." J Interv Cardiac Electrophysiol, 2:285-292 (1998).
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Gelfand, M., et al., "Treatment of renal failure and hypertension." U.S. Appl. No. 60/442,970.
Han, Y.-M, et al., "Renal artery ebolization with diluted hot contrast medium: An experimental study." J Vasc Interv Radiol, 12: 862-868 (2001).
Huang et al., "Renal denervation prevents and reverses hyperinsulinemia-induced hypertension in rats." Hypertension 32 (1998) pp. 249-254.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Lustrgarten, D.L.,et al., "Cryothermal ablation: Mechanism of tissue injury and current experience in the treatment of tachyarrhythmias." Progr Cardiovasc Dis, 41:481-498 (1999).

Oliverira, V., et al., "Renal denervation normalizes pressure and baroreceptor reflex in high renin hypertension in conscious rats." Hypertension, 19:II-17-II-21 (1992).
Opposition to European Patent No. EP2092957, Granted Jan. 5, 2011, Date of Opposition Oct. 5, 2011, 26 pages.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Peet, M., "Hypertension and its Surgical Treatment by bilateral supradiaphragmatic splanchnicectomy" Am J Surgery (1948) pp. 48-68.
Schauerte, P., et al. "Catheter ablation of cardiac autonomic nerves for prevention of vagal atrial fibrillation." Circulation, 102:2774-2780 (2000).
Smithwick et al., "Splanchnicectomy for essential hypertension." J. Am. Med. Assn. 152:16 (1953), pp. 1501-1504.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal deneravation on haemodynamic and excretory functions on the ipsilateral and contralateral kidney in the cat." Hypertension, 4:181-188 (1986).
Swartz, J.F., et al., "Radiofrequency endocardial cateheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Valente, J.F. "Laparoscopic renal denervation for intractable ADPKD-related pain." Nephrol Dial Transplant, 16: 160 (2001).
Weinstock, M., et al., "Renal denervation prevents sodium rentention and hypertension in salt sensitive rabbits with genetic baroreflex impairment." Clinical Science, 90:287-293 (1996).
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardian Electrophysiology, 2001, pp. 401-410.
Hall, W. H., et al. "Combined embolization and percutaneous radiofrequency ablation of a solid renal tumor." Am. J. Roentgenol,174: 1592-1594 (2000).
Hanson, J. M., et al. "The transplanted human kidney does not achieve functional reinnervation." Clin. Sci, 87: 13-19 (1994).
Hendee, W. R. et al. "Use of Animals in Biomedical Research: The Challenge and Response." American Medical Association White Paper (1988).
Medical-Dictionary.com, Definition of "Animal Model," http://medical-dictionary.com (search "Animal Model"), 2000.
Ong, K. L., et al. "Prevalence, Awareness, Treatment, and Control of Hypertension Among United States Adults 1999-2004." Hypertension, 49: 69-75 (2007) (originally published, online Dec. 11, 2006).

* cited by examiner

SYSTEMS AND METHODS FOR NEUROMODULATION FOR TREATMENT OF PAIN AND OTHER DISORDERS ASSOCIATED WITH NERVE CONDUCTION

CROSS-REFERENCES TO RELATED APPLICATIONS

This application is a continuation of U.S. application Ser. No. 11/459,582, filed on Jul. 24, 2006, which claims the benefit of Provisional Application No. 60/701,747, filed Jul. 22, 2005, the full disclosures of which are incorporated herein by reference.

BACKGROUND

Field of the Invention

The present invention relates to methods and apparatus for the treatment of nerve function, and more particularly, for selective disruption of conduction pathways in the body for the treatment of pain and other disorders associated with nerve conduction in various regions within the body.

Approximately 50 million Americans suffer with persistent (chronic) pain. The number of people suffering with chronic pain is higher than the number suffering from serious or terminal illnesses. Yet, unlike major illnesses, most chronic pain is untreated or under-treated. Pain surveys report that 42% of those experiencing chronic pain have such severe pain that they are unable to work, and 63% of pain sufferers are unable to engage in the routine activities of daily life. It has been estimated that among active workers, the loss of productivity from common pain syndromes costs over 60 billion dollars annually. In recent years, consumer advocacy, demographics, and advances in pain control technology have highlighted the clinical need for solutions and advanced the practice of pain management to a priority for healthcare providers.

Irreversible surgical ablation has been relied upon for the treatment of chronic pain. Lesions are placed on or in the peripheral nerves, spinal chord or brain, but such placement can have side effects such as unintended motor system effects, and required open, surgical procedures. More recently, reversible electrical and localized pharmacologic solutions started to be used.

Electrical techniques, such as neurostimulation, which deliver a low voltage electrical stimulation to a targeted peripheral nerve or spinal chord to essentially block the sensation of pain as recognized by the brain. First used in the 1960's, electrical stimulation of the peripheral nerves was shown to mask pain with a tingling sensation (paresthesia). This mechanism is part of the "gate control theory of pain" (Melzack and Wall, Science (1965) 150: 971-979.), proposing that a "gate" exists in the spinal chord that controls the transmission of pain signals to the brain. The theory suggests that activation of certain nerve fibers in the dorsal horn of the spinal chord can "close the gate" thereby inhibiting or muting the pain signals.

A variety of different electrical stimulation techniques have been employed to achieve such blocking of the pain signals, including Transcutaneous Electrical Nerve Stimulation (TENS) which provides non-invasive (skin surface) electrical stimulation to the large mylenated fiber spinal afferents, which functionally blocks nerve signal transmission to essentially create a "short circuit" between the nerve fibers and the sensory pathway to the brain. TENS may be applied to peripheral nerve stimulation, as well as spinal chord stimulation utilizing electrodes placed at the site of the targeted nerve.

In addition, a technique utilizing stronger electrical stimulation applied to acupuncture needles placed beneath the skin, referred to as Electroacupuncture or Acupuncture Like Transcutaneous Nerve Stimulation (ALTENS), has been employed with the goal of optimizing the release of endorphins and serotonin to combat pain. Various electrical stimulation devices are described in U.S. Pat. Nos. 4,573,481, 3,911,930 and 4,141,365, each of which is hereby incorporated by reference in their entirety.

The LISS Cranial Stimulator (LCS) and the LISS Body Stimulator (LBS) which deliver a monopolar current at a frequency of 15,000 Hz, modulated at 50 ms "on" and 16.7 ms "off" has been used for pain treatment. (Liss, et al., (1996) Behavioral Science 31: 88-94) U.S. Pat. Nos. 5,983,141 and 6,246,912 to Sluijter describe the application of an electromagnetic signal to neural tissue for pain relief through an electrode to alter the function of the tissue without causing temperatures that are lethal to the tissue.

Stimulation of the sensory thalamus and periaqueductal or periventricular gray in the deep brain has also shown promise in treating patients that have not been helped by other less invasive modalities of treatment. In this approach, electrodes are placed in the targeted regions of the brain under stereotactic guidance. Stimulation is then applied and when a satisfactory results is achieved, a signal generator may be implanted for long term use. A variety of severe side effects can result from this approach however, including intracerebral hemorrhage and life threatening infections.

Another approach used widely is orally administered opiates and narcotics, however the systemic effect and addictive nature of the oral medications make them less likely to provide a long term solution. Localized drug delivery or intraspinal drug administration has also shown promise, due to the fact that the approach requires significantly lower doses of narcotics that are delivered directly to the targeted region of the spinal chord either through epidural or intrathecal administration. In these approaches, percutanous catheters may be placed at the target region, and attached to implantable (subcutaneous) reservoirs or pumps, or external drug pumps. Even though the narcotics are localized, side effects may still present, including impairment of motor function, nausea, constipation, ulcers and other side effects attendant oral narcotic administration.

Various technologies are currently marketed to treat pain and other motor dysfunctions. Advanced Neuromodulation Systems (Plano, Tex.) manufactures an RF transmitter and probe for spinal chord stimulation as well as an implantable drug delivery system to relieve chronic pain, the latter being described in U.S. Pat. No. 5,938,690, hereby incorporated by reference in its entirety. Vertis Neuroscience (Vancouver, Wash.) provides externally placed, targeted electrode arrays that provide stimulation to the upper and lower back to provide relief to chronic pain referred to as Percutaneous Neuromodulation Therapy (PNT™). Synaptic Corporation (Aurora, Colo.) provides a product for external stimulation for chronic pain by creating electrical impulses along specific sensory nerve pathways to inhibit pain signals to the brain, effect tissue healing, and produce general tissue anesthesia, as further depicted in U.S. Pat. No. 6,161,044, hereby incorporated by reference in its entirety. US2004/0186532 describes an electrode implantable in the brain stem to deliver electrical stimulation to treat pain.

Additional implantable systems include, a rechargeable spinal chord stimulation system that includes an implantable pulse generator and leads attached to various regions of the spine that are connected to an external remote control or alternative charging system. Such systems are available from Advanced Bionics, a division of Boston Scientific, Natick, Mass. and from Medtronic, Inc. Minneapolis, Minn. Such systems are described in U.S. Pat. No. 6,847,849. The Medtronic system may also include drug delivery technology including intrathecal drug delivery.

Although promising, many of these systems do not provide a lasting effect, and for some, the therapeutic effect is only felt while the therapy is being administered. The treatment of intractable chronic pain remains a challenge.

In light of the foregoing, it would be desirable to provide methods and apparatus for treating pain and other disorders associated with nerve conductivity within the human body. The methods and apparatus preferably are minimally invasive or non-invasive, are targeted to specific tissue, such as nerve tissue, and provide a long therapeutic effect. It would further be desirable to provide devices and methods that modify nerve function without necessarily causing permanent physical nerve damage (neuralgia) that can occur once the treated nerve regenerates. At least some of these objectives will be met by the inventions described below.

All publications and patents or patent applications mentioned in this specification are herein incorporated by reference to the same extent as if each individual publication, patent or patent application was specifically and individually so incorporated by reference.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

The present invention provides methods and apparatus for treating pain and other nerve related disorders where the methods and apparatus are minimally or non-invasive, controlled and selective, and/or offer a more durable effect.

Methods and apparatus according to the present invention treat chronic pain and other neural defects by delivering energy to disrupt nerve tissue at the cellular level to cause permeabolization (poration) of the cell membrane to affect the viability of the nerves at the targeted region. Target nerves include nerves in the spine, particularly cervical, thoracic, lumbar and sacral regions of the spine; peripheral nerves; nerves of the head and neck; and the brain stem. Depending on the amplitude and duration of the applied field, the "poration" of the target nerve may be reversible or irreversible, as desired. Reversible electroporation may be used in conjunction with a nerve blocking agent, chemical or other therapeutic agent to enhance, modify or otherwise modulate disruption of the nerves and/or targeted tissue.

In one aspect of the present invention methods and apparatus are provided for treating chronic pain and other neural defects by delivering an electric, ultrasonic or other energy field generated by a pulse or pulses of a designated duration and amplitude to disrupt nerve or other tissue at the cellular level via permeabolization of the cell or cell membrane.

In a further aspect of the invention, the energy may be delivered under conditions selected to cause irreversible cell damage by the creation of pores in the cell membrane which result in the death of the cell. Alternatively, the conditions may be selected to cause reversible or partially reversible cell damage.

In another aspect of the invention, intracellular electromanipulation of the targeted tissue (such as nerve tissue) using ultrashort electric field pulses leading to apoptosis of the targeted cell may be desirable.

A further aspect of the invention is to provide methods and apparatus for treating chronic pain and other neural defects by utilizing an electric field to disrupt tissue at the cellular level via permeabolization of the cell causing reversible electroporation of the cellular membrane, preferably by delivering an electric pulse or chain of pulses having a voltage between 40V and 1,000,000V. Such reversible electroporation may be applied in conjunction with a therapeutic agent such as a nerve blocking agent, a neurotoxin or neurotoxin fragment, such as the light chain portion of botulinim toxin serotype A.

In a further aspect of the invention, it may be desirable to provide methods and devices that selectively disrupt certain cell types and not others, to provide a therapy that can be applied from multiple locations within the body.

In a preferred aspect of the present invention, the target nerves are frequently located adjacent to arteries which can be used for percutaneous access to the nerves. for example, vascular catheters having electrodes, ultrasonic transducers, or other energy sources at their distal ends may be advanced through an artery to an arterial site adjacent to the target nerve which often runs directly along the outside of the artery. energy can be applied which denervates the nerve while leaving the arterial wall intact as the nerve cells are more susceptible to injury. Thus, a single treatment can damage the adjacent nerve for extended periods of months or more without damaging the artery used for access.

Examples of arteries that can be used to access particular target nerves of the body regions include:

| Artery | Nerve |
| --- | --- |
| Carotid | Cranio-facial |
| Vertebral | Cranio-facial |
| Radial | Peripheral (Arms and Hands) |
| Femoral | Lower limbs, Sciatica, Disc Pain |
| Popliteal | Lower limbs, Sciatica, Disc Pain |

In a specific aspect of the present invention, patients suffering from refactory angina may be treated by reversible or irreversible disruption of the stellate ganglion in the neck in the area of the C6 vertebra (FIG. 1B) and/or of the paravertebral nerves in the spine in the area of the T6 vertebra (FIG. 1B). The stellate ganglion and associated nerves can be treated or denervated by passing a nerve poration catheter into the common, internal or external arteries, placing the treatment electrode(s) or other component adjacent the nerve level to be treated, and delivering energy to cause irreversible poration to the target nerves. Some nerves may be better accessed via catheter placement in the vertebral or subclavian arteries. Nerves in the area of T6 can be accessed by placing the treatment catheter in the aorta, anterior or posterior spinal arteries, radicular arteries, intercostal arteries, or medullary arteries.

The examples of arteries accessed and nerves treated to address various pain syndromes should be considered exemplary in nature and not limiting. It should be recognized that any syndrome which is amenable by treatment by denervation will be amenable to treatment via by the inventive technology.

For a fuller understanding of the nature and advantages of the present invention, reference should be made to the ensuing detailed description and accompanying drawings.

BRIEF DESCRIPTION OF THE DRAWINGS

Further features of the invention, its nature and various advantages will be more apparent from the accompanying drawings and the following detailed description, in which.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

The present invention is directed to methods and apparatus for targeting, stimulating, and disrupting nerve tissue, or tissue adjacent nerve tissue (collectively "target tissue") usually at the cellular level, in order to selectively denervate or disrupt nerves and nerve pathways responsible for creating a pain response in a mammalian body. Target tissue may be treated from one or more locations either adjacent to or at a distance from target tissue. The target tissue may include the nerve directly associated with the pain response and/or conduction pathways contributing directly or indirectly to the pain response.

Pain syndromes that may be treated utilizing the present invention include, neuropathic and nociceptive pain, for example, musculoskeletal pain (back, neck shoulder), myofascial (muscle) pain, neuropathic pain (complex regional pain syndrome, central pain syndrome, neuralgia, neuropathy), headaches, cancer pain, fibromyalgia, pelvic pain, arachnoiditis, arthritis, facial pain (TMJ, Temporomandibular disorders (TMD)), sciatica, skin disorders (burn pain, shingles, herpes, tumors, vasculitis), spacicity, spinal chord injury or stenosis, sickle cell disease, and pain associated with vascular disease, both peripheral and cardiac.

The body's nervous system consists of the central nervous system (brain), spinal chord nerves and the peripheral nervous system (sensory nerve fibers and motor nerve fibers outside of the brain and spinal chord). The system includes nerves (bundles of axons enclosed in connective tissue) and can be characterized as sensory/afferent, motor/efferent, or a combination of both sensory and motor fibers. The spinal nerves include fused nerve roots, for example, the dorsal root nerves are associated with sensory functions, and the ventral root nerves are associated with motor functions. Peripheral nerves may be cranial (arising from the brain), or spinal (arising from the spinal column), and are usually associated with sensations or motor functions in the hands, arms, legs or feet.

Figure 1A:
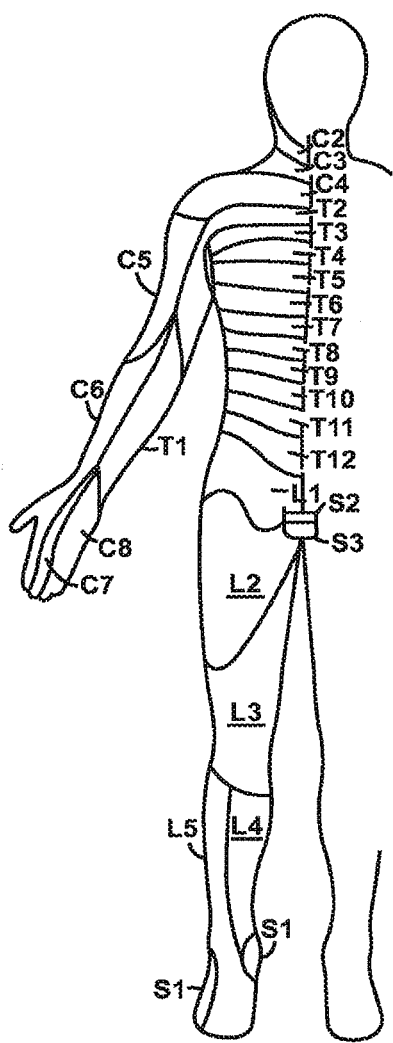
FIG. 1A—depicts a Dermatome showing areas of the body (skin) supplied by corresponding nerve fibers on front of body.
Figure 1B:
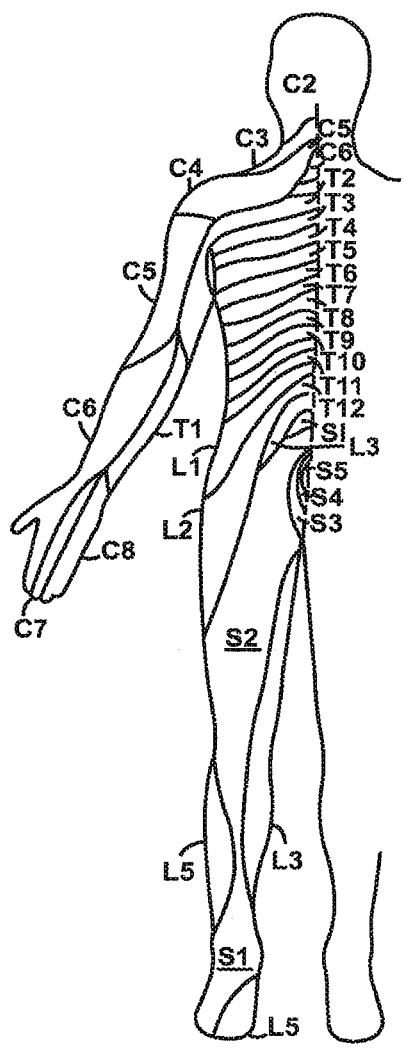
FIG. 1B—depicts a Dermatome showing areas of the body (skin) supplied by corresponding nerve fibers on rear of body.
Figure 2:
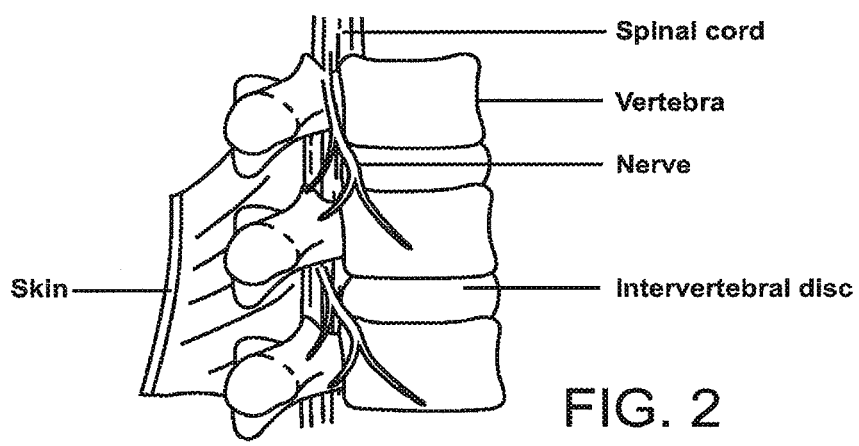
FIG. 2—depicts a side view of three vertebrae in a vertebral column showing certain relationships between spinal nerve roots and vertebrae.

Cranial nerves are mostly associated with motor function, or a combination of motor and sensory functions. As shown in FIG. 2, the spinal nerves consist of 31 pairs of nerves organized into various regions along the spine the cervical (C), thoracic (T), lumbar (L), and sacral (S). The spinal nerves are further organized into nerve networks or nerve plexus including C1-C4 (cervical plexus), C5-C8 and T1 (brachial plexus), L1-14 (lumbar plexus), and L4-S4 (sacral plexus). The relationship between the spinal nerve and the muscle (myotome) and between spinal nerve and skin (dermatome) are depicted in FIGS. 1A and 1B, showing the nerves associated with the particular region of the body. In treating pain or other disorders associated with nerve conduction in the body, devices can target a relatively localized region of the spinal column depending on the type of pain or motor function and location of pain or motor function (dermatome or myotome) to be treated.

Devices of the present invention may be directed to "targeted regions" such as cervical, thoracic, lumbar and sacral regions of the spine, peripheral nerves, nerves of the head and neck, brain stem, and deep brain. Some particular examples include, spinal chord modulation for chronic pain (for example application of energy of the present invention to the region of the spine at L1-L5 to treat lower limb and/or back pain), peripheral nerve modulation for chronic pain (for example the radial or ulnar nerve to treat hand or finger pain or dysesthesias.), and sacral nerve modulation to treat pelvic pain. In some instances, the devices and methods of the present invention may also be employed to treat certain motor dysfunctions; for example, spinal chord nerve modulation to treat peripheral vascular disease (PVD), deep brain nerve modulation for tremor, Parkinsons, depression, obsessive compulsive disorder, motor dysfunction, and brain injury, and vagus nerve modulation for treatment of epilepsy, or obesity.

High Voltage Pulsed Electric Fields. To achieve the goals of the present invention, it may be desirable to employ methods and apparatus for achieving nerve modulation and/or denervation utilizing pulsed electric fields and/or electroporation applied directly to the targeted region or in proximity to the targeted region to produce the desired denervation or nerve disruption. For purposes of this disclosure, the term "electroporation" can encompass the use of pulsed electric fields (PEFs), nanosecond pulsed electric fields (nsPEFs), ionophoreseis, electrophoresis, electropermeabilization, sonoporation and/or combinations thereof, permanent or temporary, reversible or irreversible, with or without the use of adjuctive agents, without necessitating the presence of a thermal effect. Similarly, the term "electrode" used herein, encompasses the use of various types of energy producing devices, including antennas (microwave transmitters) and ultrasonic elements. In practice, sonoporation, cell membrane manipulation by application of ultrasonic energy, may have advantages in performing the therapeutic treatment of the present invention due to its ability to manipulate the membrane without producing as much heat at the treatment site as other energy modalities that have been used, and its ability to focus at a specific treatment site.

The methods and apparatus of the present invention can employ reversible electroporation of the type used in medicine and biology to transfer chemicals, drugs, genes and other molecules into targeted cells for a variety of purposes such as electrochemotherapy, gene transfer, transdermal drug delivery, vaccines, and the like. Irreversible electroporation may also be employed as used for cell separation in debacterilization of water and food, stem cell enrichment and cancer cell purging (U.S. Pat. No. 6,043,066 to Mangano), directed ablation of neoplastic prostate tissues (US2003/0060856 to Chomenky), treatment of restenosis in body vessels (US2001/0044596 to Jaafar), selective irreversible electroporation of fat cells (US 2004/0019371 to Jaafar) and ablation of tumors (Davalos, et al. *Annals of Biomedical Engineering* 33: 223-321. The entire contents of each of these references are expressly incorporated herein by reference.

Energy fields applied in ultrashort pulses, or nanosecond pulsed electric fields (nsPEFs) may also be used to porate target nerve and other cells in accordance with the present invention. Ultrashort pulse lengths are directed at target subcellular structures without permanently disrupting the outer membrane. An example of this technology is described by Schoenbach et al. (2001) *J. Bioelectromagnetics* 22: 440-448, and in U.S. Pat. No. 6,326,177, the contents of which is expressly herein incorporated by reference. The short pulses target the intracellular apparatus, and although the cell membrane may exhibit an electroporative effect, such effect is reversible and does not lead to permanent membrane disruption. Following application of nanosecond pulses, apoptosis is induced in the intracellular contents, affecting the cell's viability (for example limiting the ability to reproduce).

In a specific embodiment of the present invention, electroporation may be achieved by energizing an electrode or series of electrodes to produce an electric field. Such a field can be generated in a bipolar or monopolar electrode configuration. When applied to cells, depending on the duration and strength of the applied pulses, this field operates to increase the permeabolization of the cell membrane and either (1) reversibly open the cell membrane for a short period of time by causing pores to form in the cell lipid bilayer allowing entry of various therapeutic elements or molecules, after which, when energy application ceases, the pores spontaneously close without killing the cell, or (2) irreversibly opening or porating the cell membrane causing cell instability resulting in cell death utilizing higher intensity (longer or higher energy) pulses, or (3) applying energy in nanosecond pulses resulting in disruption of the intracellular matrix leading to apoptosis and cell death, without causing irreversible poration of the cellular membrane. As characterized by Weaver (1993), *Journal of Cellular Biochemistry* 51: 426-435, short (1-100 µs) and longer (1-10 ms) pulses have induced electroporation in a variety of cell types. In a single cell model, most cells will exhibit electroporation in the range of 1-1.5 V applied across the cell (membrane potential).

Certain factors determine how a delivered electric field will affect a targeted cell, including cell size, cell shape, cell orientation with respect to the applied electric field, cell temperature, distance between cells (cell-cell separation), cell type, tissue heterogeneity, properties of the cellular membrane and the like. Larger cells may be more vulnerable to injury. For example, skeletal muscle cells have been shown to be more susceptible to electrical injury than nearby connective tissue cells (Gaylor et al. (1988) *J. Theor. Biol.* 133: 223-237). In addition, how cells are oriented within the applied field can make them more susceptible to injury, for example, when the major axis of nonspherical cells is oriented along the electric field, it is more susceptible to rupture (Lee et al. (1987) *Plastic and Reconstructive Surgery* 80: 672-679.)

Various waveforms or shapes of pulses may be applied to achieve electroporation, including sinusoidal AC pulses, DC pulses, square wave pulses, exponentially decaying waveforms or other pulse shapes such as combined AC/DC pulses, or DC shifted RF signals such as those described in Chang, (1989) *Biophysical Journal* October 56: 641-652, depending on the pulse generator used or the effect desired. The parameters of applied energy may be varied, including all or some of the following: waveform shape, amplitude, pulse duration, interval between pulses, number of pulses, combination of waveforms and the like.

Figure 4:
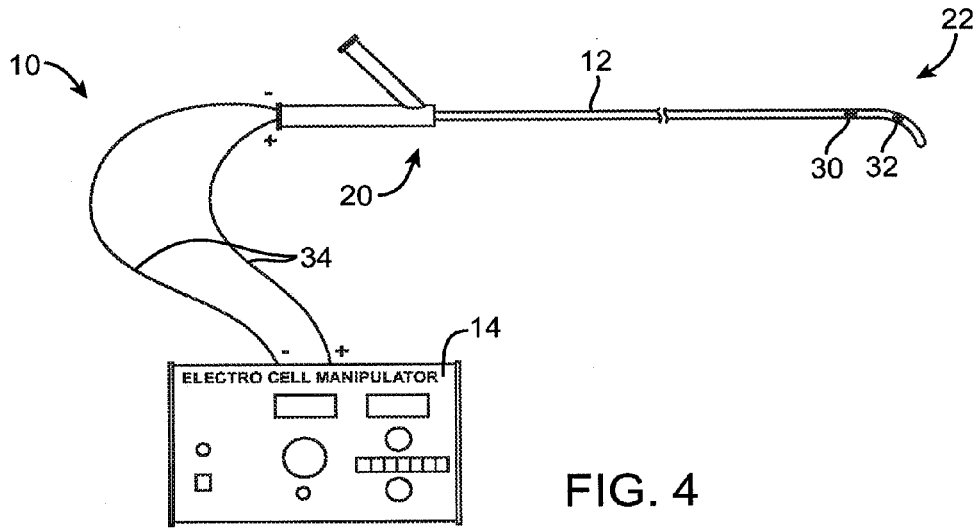
FIG. 4—depicts a generator and catheter system capable of supply pulsed electric fields to effect reversible or irreversible electroporation in targeted cells.
Figure 3:
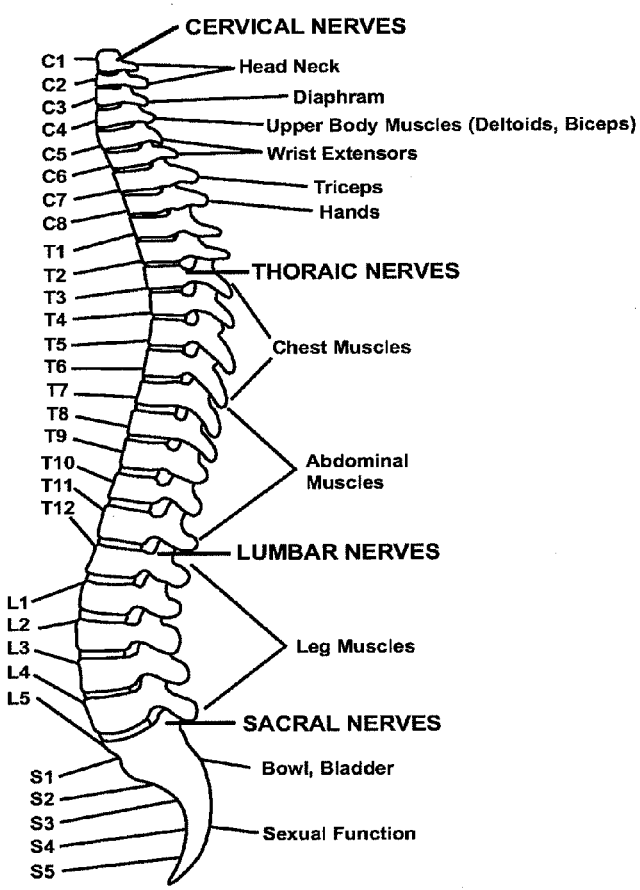
FIG. 3—depicts a schematic of spinal nerve and vertebrae.
Figure 4A:
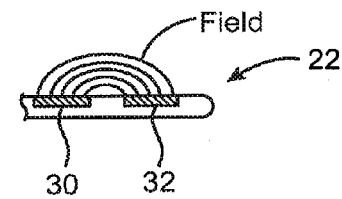
FIGS. 4A and 4B—depict catheter distal tips of the present invention in various configurations showing spaced apart electrodes, including an optional monitoring electrode.
Figure 4B:
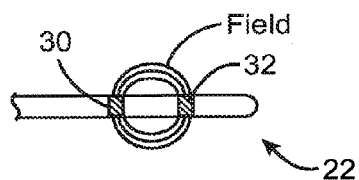

Catheter Devices. FIGS. 4 and 4A-4B depict a system 10 comprising an electroporation catheter 12 for selective denervation/disruption of nerve tissue. For purposes of this specification, the term "catheter" may be used to refer to an elongate element, hollow or solid, flexible or rigid and capable of percutaneous introduction to a body (either by itself, or through a separately created incision or puncture), such as a sheath, a trocar, a needle, a lead. In certain configurations of the present invention, voltages may be applied via the electroporation catheter 12 to induce irreversible electroporation, without requiring the use of any other agents to achieve the desired cell destruction and/or denervation. It is a further advantage of this type of energy that any thermal effect may be minimized thereby preventing or minimizing collateral damage to tissues near the target tissues, or the type of physical damage to the nerves themselves that can lead to permanent neuralgia when the nerve fibers generate A further advantage of this type of energy is that the electroporation or electropermeabilization effect is largely cell-size specific. That is, larger cells will be porated (either reversibly or irreversibly) at lower energy levels than smaller cells. This will allow the denervation effect to be directed at the relatively large nerve cells while sparing smaller adjacent cell types. In addition, the electric field may be controlled by the size and relative positioning of the electrodes on the treatment device or patient.

The electroporation catheter system 10 further comprises a pulse generator 14 such as those generators available from Cytopulse Sciences, Inc. (Columbia, Md.); Bio-Rad, Inc. (Hercules, Calif.) (the Gene Pulser Xcell); and IGEA (Carpi, Italy). The pulse generator is electrically connected to the catheter 12 which has a proximal end 20 and a distal end 22 and is adapted for either surface placement (cutaneous) or minimally invasive insertion into the desired region of the body as described herein. The generator 14 may be modified to produce a higher voltage, increased pulse capacity or other modifications to induce irreversible electroporation. The catheter 12 further comprises an electroporation element at the distal end thereof comprising a first electrode 30 and a second axially spaced-apart electrode 32 operatively connected to the pulse generator through cables 34 for delivering the desired number, duration, amplitude and frequency of pulses to affect the targeted nerve tissue. The energy delivery parameters can be modified either by the system or the user, depending on the location of the catheter within the body (e.g., the nature of the intervening tissues or structures) and whether a reversible or irreversible cell poration is desired. For example energy in the range of 10 V/cm to $10^4$ V/cm for a duration of 10 μs to 100 ms may be used to achieve reversible electroporation and in the range of 100 V/cm to $10^6$ V/cm for a duration of 10 μsec to 100 msec to achieve irreversible electroporation or apoptosis. As shown in FIG. 4A, electrodes 30 and 32 may be axially aligned on one side of catheter 12 to produce an electric field concentrated in a lateral direction from the catheter body. Using ring electrodes 30 and 32 as shown in FIG. 4B, creates a more uniform electric field about the shaft of the catheter 12. Additional monitoring electrode(s), may be located on the catheter 12.

Figure 5A:
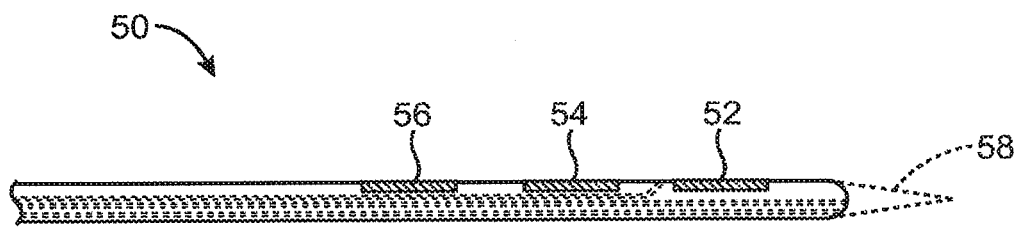
FIGS. 5A-D—depict various electrode catheter configurations adapted to deliver energy or energy and therapeutic agents to target tissue.

Further catheter devices and electrode configurations are shown in FIGS. 5A-5D. FIG. 5A depicts an elongate catheter 50 having a first electrode 52 and second electrode 54 near its distal tip. A monitoring or stimulation electrode 56 is disposed in the vicinity of the porating electrodes 52 and 54 for monitoring or localizing the treatment area. In some embodiments, the monitoring or stimulating function may be performed by one or more of the treatment electrodes. The catheter 50 may have an optional sharp tip 58 (shown in broken line) to facilitate percutaneous introduction. Electrodes 52, 54 and 56 are shown as axially aligned on one side of the catheter 50 but could also have ring or other structures.

Figure 5B:
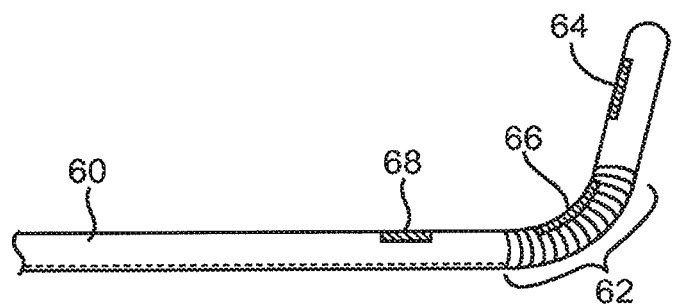

FIG. 5B illustrates a steerable catheter 60 adapted to bend or articulate at a region 62 near its distal end. Active electrodes 64 and 66 are disposed adjacent to or within the articulated region 62 and a monitoring or stimulation electrode 68 is optionally disposed proximally of the active electrodes. Such steering ability enables the operator to introduce the device into tight or tortuous spaces so that optimal placement of the device may be achieved.

Figure 5C:
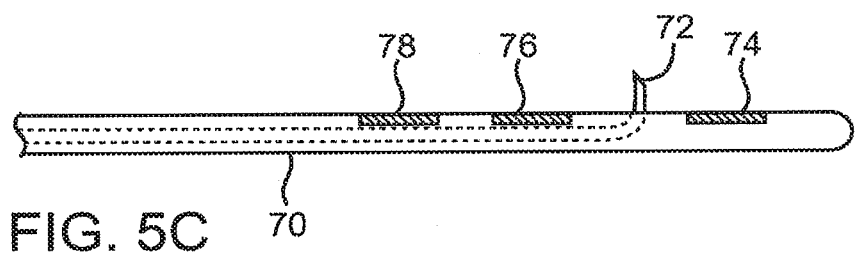

FIG. 5C depicts a catheter 70 that includes an injection element 72 to allow for the injection of a therapeutic agent before, during or after the application of the pulsed energy or electroporation from active electrodes 74 and 76 and monitoring or stimulating electrode 78. The injection element may be a needle as shown in FIG. 5C, an infusion port, or other infusion means. Such a therapeutic agent may be, for example, lidocaine, botulinum toxin (either full or in fragment as detailed copending application Ser. No. 11/459,090, filed on Jul. 21, 2006, the full disclosure of which has been incorporated herein by reference), capsaicin or a variety of nerve blocking agents. The use of the devices and methods of the present invention can increase the effectivity and provide for alternative means of delivery for botulinum toxin to treat pain by inhibiting the release of the neurotransmitter responsible for the transmission of pain, such as various neuropathic diseases and disorders as described in U.S. Pat. Nos. 6,113,915, 6,333,037, 6,372,226, 6,841,156, 6,896,886 and 6,869,610 to Aoki, the contents of which are expressly incorporated herein by reference in their entirety. Further, to aid the electroporation process, it may be advantageous to heat the targeted cells or surrounding tissue by either applying thermal energy directly to the region, or directing a heated fluid, such as saline to the region through the injection element.

Figure 5D:
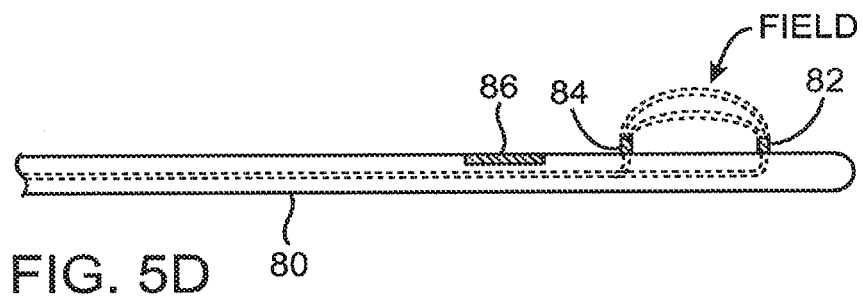

FIG. 5D depicts a catheter 80 having deployable electrode elements 82 and 84 that are adapted to extend laterally from the main catheter body, and in some cases, penetrate the surrounding tissue prior to application of energy. In doing so the depth and direction of the energy field created by the electroporative process, may be further controlled. As with the previous embodiments, a stimulating or monitoring electrode 86 may optionally be provided proximally of the active electrodes.

In certain configurations it may be advantageous to use the poration catheters and methods of the present invention in conjunction with a nerve blocking agent, neurotoxin, neurotoxin fragment or other therapeutic agents according to methods and devices described in co-pending patent application Ser. No. 11/459,090, filed on Jul. 21, 2006, the full disclosure of which has been incorporated by reference in its entirety. In this instance, the voltage applied to the electrode elements would preferably be in the range applicable to create a reversible electroporation of the nerve or tissue cells, thereby porating the cell to allowing the therapeutic agent to be delivered to achieve the desired effect, but not destroying the cell or otherwise irreversibly damaging the targeted tissue or nerve structures.

Any of the foregoing systems may include electrodes or other monitoring systems either located on the treatment catheter, or external to the patient, to determine the degree of treatment to the region, including, thermocouple, ultrasound transducers, fiberoptics, sensing or stimulating electrodes. Further, it may be desirable to incorporate multiple pairs of electrodes that may be activated in pairs, in groups, or in a sequential manner in order to maximize the desired shape of the lesion while minimizing the field strength requirements. Also, the devices of the present invention may be used in conjunction with more traditional neuromodulation techniques, such as TENS, to mediate pain attributable to the treatment (the presence of which may depend on the level of voltage applied) or neuromuscular response to the applied electric field as further noted in published U.S. Application No. 2003/0149451, hereby incorporated by reference in its entirety.

Figure 6:
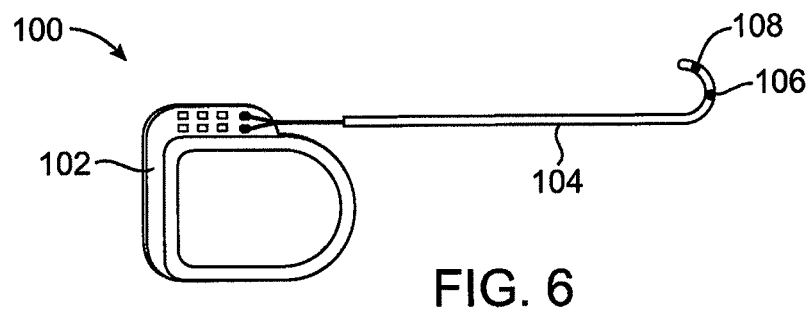
FIG. 6—depicts a fully implantable pulse generator and lead of the present invention.
Figure 7:
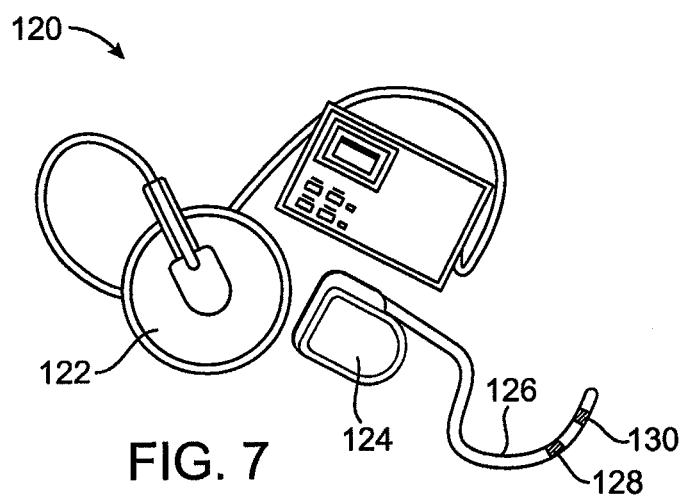
FIG. 7—depicts an implantable receiver and external transmitter and controller for delivering energy according to the present invention.
Figure 8:
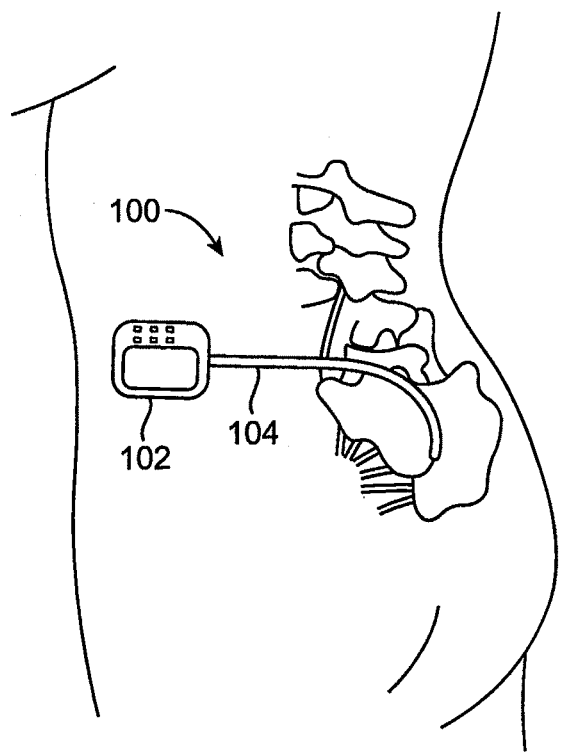
FIG. 8—depicts a schematic representing placement of the implantable version of the present invention.

Implantable Devices. A fully implantable spinal cord modulation system 100 includes an implantable pulse generator 102 which incorporates a power supply or battery as depicted in FIG. 6. The system 100 connects to an implantable lead 104 which includes electrodes 106 and 108. As shown in FIG. 7, a partially implantable system 120 includes a transmitter 122, and a receiver 124 that relies upon radio frequency to transmit the energy to the lead or electrode. In this system the antenna and transmitter are carried outside the body, while the receiver connected to the lead 126 with electrodes 128 and 130) is implanted inside the body. FIG. 8 shows the placement of the fully implantable pulse generator 100 device in the region of the sacral plexus of a patient which has been implanted according to the steps set forth in U.S. Pat. No. 6,847,849, previously incorporated by reference herein. Implantation of the partially implantable system 120 could be achieved in the identical manner.

Figure 9A:
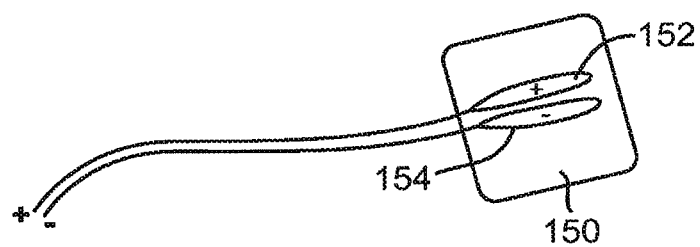
FIGS. 9A and B—depict an electrode pad for placement on the skin of a patient, including one or multiple circuits, either smooth or incorporating microneedles.
Figure 9B:
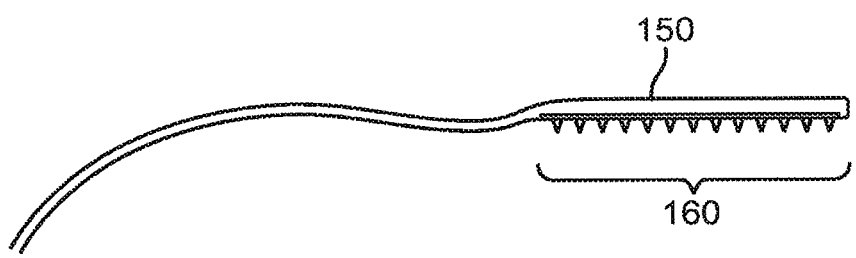

Cutaneous or Subcutaneous Devices. For some conditions, it may be desirable to apply the poration energy from the surface of the skin (transcutaneously), or from just below the skin (subcutaneously). FIG. 9A depicts a dermal patch 150 having an electrode pair 152 and 154 for delivery of therapeutic energy of the present invention to the targeted region. Alternatively, the pad may include one electrode, while the other (a ground) may be positioned elsewhere on the patient's skin (not shown). Depending on the type of voltage applied and condition to be treated, it may be desirable to have multiple electrode pairs on the surface of the patch or pad, and in some cases as shown in FIG. 9B, such electrodes may be in the form of microneedles 160 that puncture the skin some distance to deliver the therapeutic energy of the present invention subcutaneously. The patch or pad carrying the electrodes should be flexible and conformable and may be formed of a polymer such as silicone, urethane, nylon, polyethylene or other thermoplastic elastomers, or could be substantially rigid and formed of a rigid polymer (such as PEEK or polysulfone) or insulated stainless steel, nickel titanium alloy, or other metal. As noted above, various monitoring devices and methods may be employed to track the progress of the therapy. Similarly, algorithms to activate pairs of electrodes or regions of the pad or patch may be employed to enhance the therapeutic effect while reducing the overall power requirements.

Intraluminal Devices. It may further be advantageous to position poration catheters through vessels in the body, particularly arteries to treat adjacent nerves, to direct poration energy to various regions to effect pain reduction. Such intraluminal catheters are described in published U.S. Applications 2001/0044596 to Jaafar and 2002/0198512 to Seward, hereby incorporated by reference in their entirety, could be used for such energy delivery.

Figure 10:
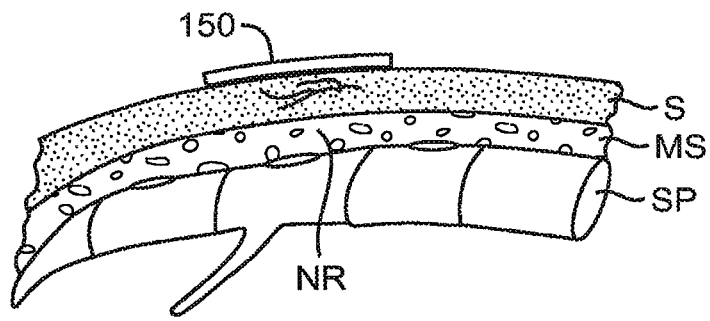
FIG. 10—depicts a method of use of the invention according to FIGS. 9A and 9B.
Figure 11:
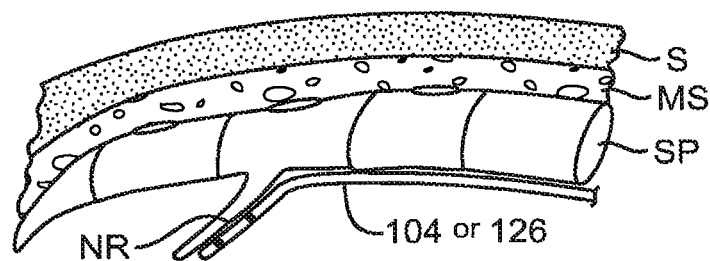
FIG. 11—depicts a method of use of the invention according to FIG. 6.
Figure 12:
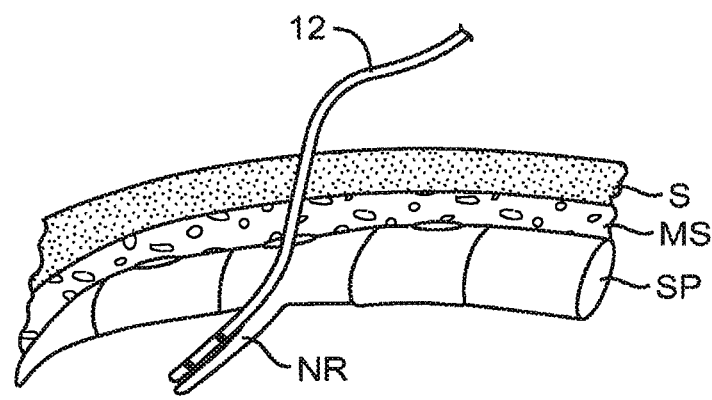
FIG. 12—depicts a method of use of the invention according to FIGS. 5A-5D.

Methods of Use. FIG. 10 illustrates a method for nerve poration by applying energy to the surface of the skin S via the electrode patch 150. FIG. 11 depicts the implantation of electrode lead 104 or 126 that is then operatively connected to the implantable generator and described herein. FIG. 12 shows percutaneous nerve poration catheter 12 implanted in a region within the spine. In FIGS. 11 and 12, the active tip region of the catheter or lead is shown placed alongside the nerve region NR to be treated, but in fact may be positioned within the nerve sheath, or along the spine (SP), or within the muscular layer (MP).

Figure 13:
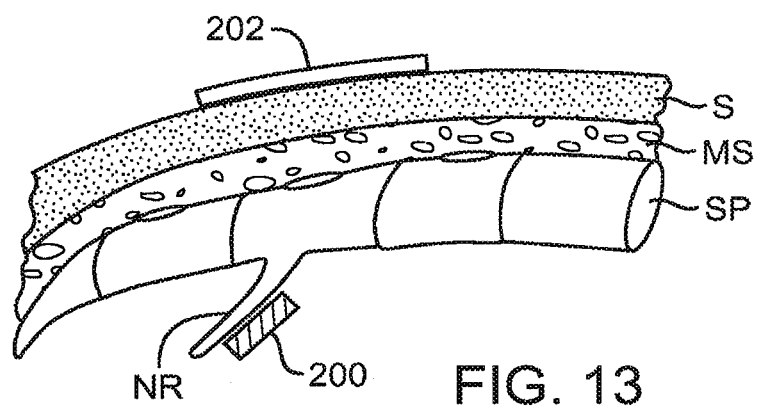
FIG. 13—depicts a method of use of the invention according to FIG. 7.

In yet another embodiment shown in FIG. 13, a receiver 200 may be placed at the target location (here alongside the nerve region NR in the spine SP), while a transmitter 202 is placed outside or on the skin of the patient. Once in place adjacent the nerve region NR to be treated, a pulse generator in the transmitter 202 may be activated, causing an electric field to be generated in the target area. Prior to activation of therapeutic voltages, once the catheter(s) have been appropriately positioned, stimulation using one or more electrodes may be used to elicit a nerve response. By observing the nerve reflex, a target treatment location can be confirmed, and then application of poration energy is employed to eliminate or disrupt the nerve and associated pain response, thereby selectively denervating the conduction pathways for the particular type of pain to be treated.

Figure 14:
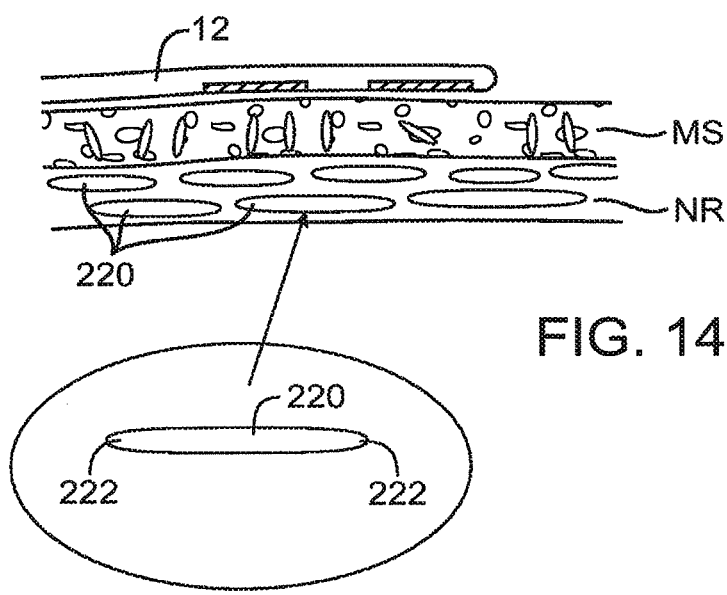
FIG. 14—depicts a schematic of a nerve fiber showing the relative cell size allowing selective cell permeabolization of nerve cells.

In operation, effects of poration on nerve tissue may be selective due to the cellular structure and orientation of the nerve cells. For example as shown in FIG. 14, targeted nerve cells may be preferentially affected due to size, sparing smaller or cross-oriented muscle tissue. As shown, the energy may selectively rupture the nerve cells 220 at ends 222 while the energy dissipates over the main body of the cells.

Figure 15:
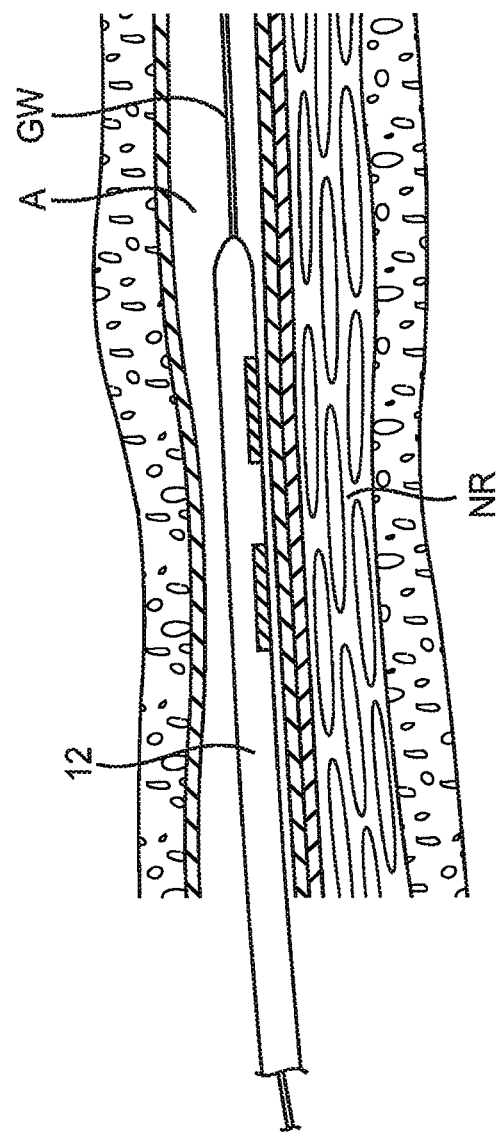
FIG. 15—depicts a schematic of a target nerve region being treated by a poration catheter in an adjacent artery.

As shown in FIG. 15, poration catheter 12 can be introduced into a lumen of artery A to a location immediately adjacent to a nerve region NR to be treated. The catheter 12 will typically be introduced over a guidewire GW under fluoroscopic guidance using well-known intravascular intervention methods and protocols. Once in place, electroporation or other poration energy can be applied across the arterial wall toward the nerve region NR to denervate the nerve as described previously. As the nerve cells will typically be more susceptible to energy induced damage, the desired temporary or permanent denervation can usually be achieved with minimum or no damage to the artery. The catheter 12 can be removed after the treatment session is completed. The treatment can be repeated months or years later if and when nerve function returns.

Although various illustrative embodiments of the present invention are described above, it will be evident to one skilled in the art that various changes and modifications may be made without departing from the scope of the invention. It will also be apparent that various changes and modifications may be made herein without departing from the invention. The appended claims are intended to cover all such changes and modifications that fall within the true spirit and scope of the invention.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. An apparatus for selective denervation of a target tissue in a patient's body, the target tissue comprising nerve cells, the apparatus comprising:
   a non-implantable intraluminal catheter configured to be percutaneously introduced into a lumen of an artery, the catheter having one or more electrodes disposed thereon, wherein the individual electrodes are configured to transmit at least one of an electrical pulse or a series of electrical pulses; and
   a pulse generator operatively connected to the catheter, wherein the pulse generator is electrically connected to a proximal end of the intraluminal catheter outside the patient's body to deliver cellular poration energy to the one or more electrodes when the catheter is percutaneously introduced into the lumen of the artery,
   wherein the electrodes and generator are configured to deliver cellular poration energy to nerve cells outside the lumen of the artery sufficient to disrupt a pain conduction pathway by inducing irreversible electroporation in the nerve cells.

2. The apparatus of claim 1, wherein the catheter is configured to be positioned percutaneously in the artery to position the one or more electrodes at a location adjacent to a region of a spine in the patient selected from the group consisting of a cervical region, a thoracic region, a sacral region and a lumbar region.

3. The apparatus of claim 1, wherein the catheter is configured to be positioned percutaneously in an artery to position the one or more electrodes at adjacent to peripheral nerves in the patient.

4. The apparatus of claim 1, wherein the pulse generator and one or more electrodes are configured to deliver poration energy at from 10 V/cm to $10^4$ V/cm for durations from 10 μsec to 100 msec.

5. The apparatus of claim 1, wherein the pulse generator and one or more electrodes are configured to deliver poration energy at from 100 V/cm to $10^6$ V/cm for durations from 10 μsec to 100 msec.

6. An apparatus for selective denervation of a target tissue of a patient, the target tissue comprising nerve cells having membranes, the apparatus comprising:
   an electrode support having one or more electrodes disposed thereon, wherein the individual electrodes are configured to transmit at least one of an electrical pulse or a series of electrical pulses; and
   a pulse generator operatively connected to the electrode support, wherein the electrodes and generator are configured to deliver cellular poration energy sufficient to disrupt a pain conduction pathway by disrupting target-tissue nerve-cell membranes and induce irreversible electroporation in the target tissue,
   wherein the support comprises a patch and the one or more electrodes are carried by the patch to be applied to skin of the patient.

7. The apparatus of claim 6, wherein the one or more electrodes comprise one or more micro needles.

8. A method for selective denervation of target tissue of a patient, the method comprising:
   delivering energy to target nerve cells of the target tissue via one or more electrodes carried by a catheter configured to be percutaneously introduced into a body lumen of the patient,
   wherein the delivered energy is sufficient to disrupt a pain conduction pathway by permeabilizing a cell membrane of the target nerve cells and inducing irreversible electroporation in the target tissue.

9. The method of claim 8, wherein the target cells are nerve cells.

10. The method of claim 9, wherein the nerve cells are peripheral nerves.

11. The method of claim 9, wherein the nerve cells are outside a lumen of an artery, and wherein delivering energy to target nerve cells comprises delivering energy from within the lumen of the artery.

12. The method of claim 11, further comprising transluminally positioning the catheter in the artery before delivering energy to the target nerve cells.

13. The method of claim 8, wherein the delivered energy is electric energy delivered in a range from 10 V/cm to $10^6$ V/cm for durations from 10 μsec to 100 msec.

14. The method of claim 8, wherein the delivered energy is electrical energy delivered in a range from 10 V/cm to $10^4$ V/cm.

15. The method of claim 8, further comprising delivering a therapeutic agent to the target tissue either before, during, or after delivering energy to the target nerve cells.

16. The method of claim 15 wherein delivering the therapeutic agent comprises delivering one or more of the following: lidocaine, botulinum toxin, capsaicin, or other nerve blocking agents.

* * * * *